United States Patent [19]

Comte et al.

[11] Patent Number: 4,999,355

[45] Date of Patent: Mar. 12, 1991

[54] ISOINDOLINONE DERIVATIVES, PROCESSES FOR PREPARING THEM AND MEDICINES CONTAINING THEM

[75] Inventors: Marie-Thérèse Comte, Chevilly Larue; Claude Gueremy, Houilles; Gérard Ponsinet, Sucy-en-Brie, all of France

[73] Assignee: Rhone-Poulenc, Antony, France

[21] Appl. No.: 319,302

[22] Filed: Mar. 6, 1989

[30] Foreign Application Priority Data

Mar. 8, 1988 [FR] France .................... 88 02918

[51] Int. Cl.$^5$ .............. A61K 31/495; A61K 31/44; C07D 403/06; C07D 401/06
[52] U.S. Cl. ................ 514/253; 514/333; 514/339; 544/373; 546/256; 546/272; 548/472
[58] Field of Search ........... 544/373; 546/273, 272, 546/256; 514/253, 339, 333

[56] References Cited

U.S. PATENT DOCUMENTS

| 3,579,524 | 5/1971 | Van Dyke | 544/373 |
| 4,505,911 | 3/1985 | Dolak et al. | 514/339 |
| 4,585,773 | 4/1986 | Dolak | 544/373 |
| 4,849,441 | 7/1989 | Okazaki et al. | 514/339 |

FOREIGN PATENT DOCUMENTS

| 1928474 | 12/1969 | Fed. Rep. of Germany . |
| 3308668 | 9/1984 | Fed. Rep. of Germany ...... 546/273 |
| 169461 | 9/1985 | Japan ............... 544/373 |
| 942866 | 11/1963 | United Kingdom .......... 544/373 |
| 2161807 | 1/1986 | United Kingdom . |

OTHER PUBLICATIONS

Corne et al., *Psychopharmacologia* 11, p. 65 (1967).
Iversen, *Neuropharmacology* 23, p. 1553 (1984).
Reyntjens et al., *Drug Development Research* 8, p. 205 (1986).
Glennon, *J. Med. Chem.* 30, p. 1 (1987).
Sandrini et al., *European Journal of Pharmacology* 130, p. 311 (1986).
Laduron in *Les Antimigaineux* (Masson Publishers) pp. 122-138 (1985).
Leysen et al., *Neuropharmacology* 23, p. 1493 (1984).
Leysen et al., *Molecular Pharmacology* 21, p. 301 (1982).
Van Dyke, *Chemical Abstracts*, vol. 72, No. 43728 (1970).
TIPS, 1987, vol. 8, p. 504.
Roelens (Dermatologica) 1989, 178, 98.
Cazzola et al., (Allergy 1990, vol. 45 (2), p. 151, Abstract).
Meuldermans et al., Arzneim. Forsch. Drug Res. 38 (I), 6, 1988.
Pharmaprojects: ZK 33 839 (Abstract).
Geller Allergy 1989, Abstract for vol. 63 (1), pp. 29–30.
Wanderer, Abstract for J. Allergy Clin. Immunol. 1986, vol. 78, p. 417.

*Primary Examiner*—Mukund J. Shah
*Assistant Examiner*—E. Bernhardt
*Attorney, Agent, or Firm*—Morgan & Finnegan

[57] ABSTRACT

Compounds of formula:

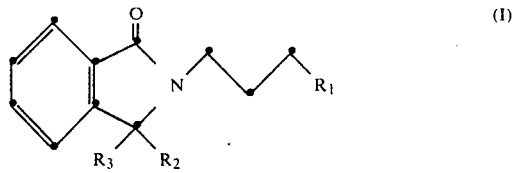

(I)

in which:
either $R_1$ represents 4-phenyl-1,2,3,6-tetrahydro-1-pyridyl or 4-(4-fluorophenyl)-1,2,3,6-tetrahydro-1-pyridyl, $R_2$ represents hydrogen, alkoxy of 1 or 2 carbon atoms, hydroxyl, alkyl, alkylthio, alkylcarbonyloxy, phenylalkylcarbonyloxy, phenylalkyl or —$NR_4R_5$ in which $R_4$ represents hydrogen or alkyl and $R_5$ represents alkyl, phenyl, monohalogenated phenyl or pyridyl, and $R_3$ represents a hydrogen atom, or else $R_2$ represent phenyl and $R_3$ represents hydrogen or hydroxyl;

or $R_1$ represnets 4-phenyl-1-piperazinyl whose phenyl nucleus has a substituent halogen atom or hydroxyl radical in the 4-position, $R_2$ represents alkoxy and $R_3$ represents hydrogen;

it being understood that when $R_1$ represents the 4-phenyl-1,2,3,6-tetrahydro-1-pyridyl radical, $R_2$ is not hydroxyl and that, unless otherwise stated, the alkyl and alkoxy radicals and the alkyl and alkoxy portions contain 1 to 4 carbon atoms each in a straight or branched chain, and addition salts thereof with an inorganic or organic acid, are useful in therapy for their serotonin antagonist properties.

14 Claims, No Drawings

ISOINDOLINONE DERIVATIVES, PROCESSES FOR PREPARING THEM AND MEDICINES CONTAINING THEM

The present invention provides, as new compounds, the isoindolinone derivatives of formula:

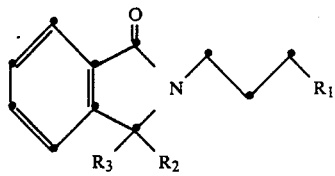
(I)

in which:
either $R_1$ represents 4-phenyl-1,2,3,6-tetrahydro-1-pyridyl or 4-(4-fluorophenyl)-1,2,3,6-tetrahydro-1-pyridyl, $R_2$ represents hydrogen, alkoxy of 1 or 2 carbon atoms, hydroxyl, alkyl, alkylthio, alkylcarbonyloxy, phenylalkylcarbonyloxy, phenylalkyl or $-NR_4R_5$ in which $R_4$ represents hydrogen or alkyl and $R_5$ represents alkyl, phenyl, monohalogenated phenyl or pyridyl and $R_3$ represents hydrogen, or else $R_2$ represents phenyl and $R_3$ represents hydrogen or hydroxyl;

or $R_1$ represents a 4-phenyl-1-piperazinyl radical whose phenyl nucleus is substituted in the 4-position by halogen or hydroxyl, $R_2$ represents alkoxy and $R_3$ represents hydrogen;

it being understood that when $R_1$ represents 4-phenyl-1,2,3,6-tetrahydro-1-pyridyl, $R_2$ is not hydroxyl, and addition salts thereof formed with an inorganic or organic acid.

Unless otherwise stated in the previous definitions and those given hereinafter, the alkyl and alkoxy radicals and the alkyl and alkoxy portions contain 1 to 4 carbon atoms each in a straight or branched chain and the halogen atoms are preferably chlorine or fluorine atoms.

The compounds of formula (I) in which $R_2$ represents an alkoxy radical and $R_1$, $R_3$ are as previously defined may be prepared by alkylation of a compound of formula:

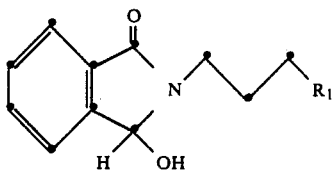
(II)

in which $R_1$ has the same meanings as in formula (I).

This alkylation is generally carried out with an aliphatic alcohol of 1 to 4 carbon atoms, in the presence of an inorganic acid such as sulphuric acid at a temperature between 20° C. and the boiling point of the alcohol.

The compound of formula (I) in which $R_2$ represents a hydroxyl radical and $R_1$, $R_3$ are as previously defined and the compounds of formula (II) that are not included in formula (I) may be prepared by reduction of a compound of formula:

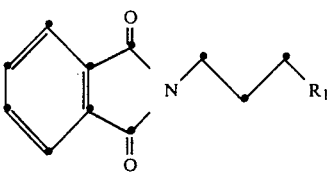
(III)

in which R represents 4-phenyl-1,2,3,6-tetrahydro-1-pyridyl, 4-(4-fluorophenyl)-1,2,3,6-tetrahydro-1-pyridyl or 4-phenyl-1-piperazinyl whose phenyl nucleus is substituted in the 4-position by halogen or hydroxyl.

This reduction is preferably carried out with an alkali metal borohydride, such as sodium borohydride or potassium borohydride, in an inert organic solvent, such as an alcohol, (e.g. methanol or ethanol), tetrahydrofuran or a mixture of such a solvent with water, at a temperature close to 20° C.

The compounds of formula (III) may be obtained by reaction of an amine of formula:

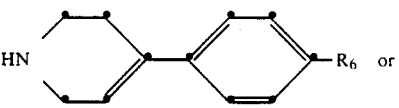
(IV)

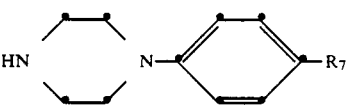
(V)

in which $R_6$ represents hydrogen or fluorine and $R_7$ represents halogen or hydroxyl, with the compound of formula:

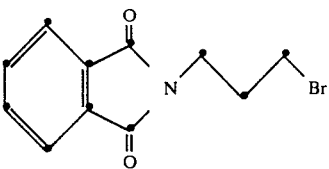
(VI)

This reaction is generally carried out in an inert aromatic solvent, such as benzene or toluene, in the presence of an acid acceptor, such as a trialkylamine, e.g. triethylamine, at a temperature between 20° C. and the boiling point of the solvent.

The compound of formula (VI) may be prepared by the process of T. O. SOINE and BUCHDAHL, Organic Synthesis, 32, 18 (1952).

The compound of formula (I) in which $R_2$ is hydroxyl and $R_1$, $R_3$ are as previously defined may also be prepared by reaction of 2-(3-bromopropyl)-3-hydroxy-1-isoindolinone with an amine of formula (IV) in which $R_6$ represents fluorine.

This reaction is generally carried out in an inert aromatic solvent, e.g. toluene, in the presence of an acid acceptor, such as a trialkylamine, e.g. triethylamine, at a temperature between 20° C. and the boiling point of the solvent.

2-(3-Bromopropyl)-3-hydroxy-1-isoindolinone may be prepared by reduction of the 2-(3-bromopropyl)phthalimide of formula (VI).

This reduction is generally carried out as previously described for the reduction of compounds of formula (III).

The compounds of formula (I) in which $R_2$ represents hydrogen and $R_1$, $R_3$ are as previously defined may be obtained by reduction of the corresponding compounds of formula (II).

This reduction is preferably carried out with zinc in the presence of an acid such as acetic acid at a temperature close to 120° C.

The compounds of formula (I) in which $R_2$ represents alkyl and $R_1$, $R_3$ are as previously defined may be prepared by reaction of a compound of formula:

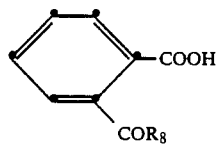
(VII)

in which $R_8$ represents , with an amine of formula:

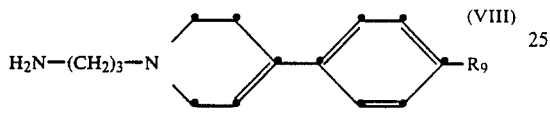
(VIII)

in which $R_9$ represents hydrogen or fluorine.

This reaction is generally carried out in the presence of sodium cyanoborohydride, in an inert organic solvent, e.g. acetonitrile, at a temperature close to 20° C.

Amines of formula (VIII) may be obtained by the action of hydrazine on a compound of formula:

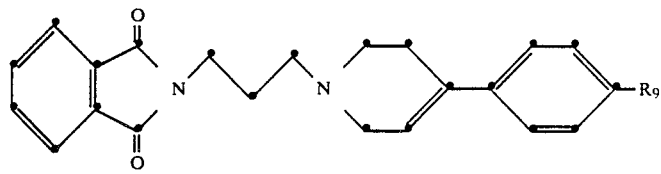
(IX)

in which $R_9$ has the same meanings as in formula (VIII).

This reaction is preferably carried out in an organic solvent such as an alcohol (e.g. methanol or ethanol) at a temperature between 20° C. and the boiling point of the solvent.

The compounds of formula (VII) may be obtained by application or adaptation of the method described by E. L. ELIEL et al., J. Am. Chem. Soc., 71, 2251 (1949).

The compounds of formula (I) in which $R_2$ represents alkylthio and $R_1$, $R_3$ are as previously defined may be prepared by reaction of methyl 2-formylbenzoate with an amine of formula (VIII) in the presence of an alkylmercaptan.

This reaction is generally carried out in an autoclave, in an inert organic solvent such as tetrahydrofuran at a temperature between 20° C. and the boiling point of the solvent, at atmospheric pressure.

The compounds of formula (I) in which $R_2$ represents alkoxy, alkylcarbonyloxy or phenylalkylcarbonyloxy and $R_1$, $R_3$ are as previously defined may be prepared by reaction of compounds of formula (II) in which $R_1$ has the same meanings as in formula (I) with a compound of formula:

$$Hal-R_{10} \quad (X)$$

in which Hal represents halogen (e.g. chlorine, bromine, or iodine) and $R_{10}$ represents alkyl, alkylcarbonyl or phenylalkylcarbonyl.

This reaction is generally carried out in the presence of a base such as sodium hydride, in an inert organic solvent such as tetrahydrofuran or dimethylformamide, at a temperature close to 20° C.

The compounds of formula (I) in which $R_2$ represents phenyl, $R_3$ represents hydroxyl and $R_1$ is as previously defined may be obtained by action of a phenylmagnesium halide such as phenylmagnesium bromide on a compound of formula (III) in which $R_1$ represents 4-phenyl -1,2,3,6-tetrahydro-1-pyridyl or 4-(4-fluorophenyl)-1,2,3,6-tetrahydro-1-pyridyl.

This reaction is generally carried out in an inert organic solvent such as tetrahydrofuran or diethyl ether at a temperature close to 20° C.

The compounds of formula (I) in which $R_2$ represents phenyl or phenylalkyl, $R_3$ represents hydrogen and $R_1$ is as previously defined may be prepared by reduction of a compound of formula:

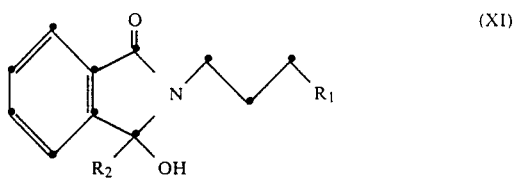
(XI)

in which $R_2$ represents phenyl or phenylalkyl and $R_1$ is defined as in formula (I).

This reduction is preferably carried out with sodium cyanoborohydride and trifluoroacetic acid at a temperature close to 20° C.

The compounds of formula (XI) in which $R_2$ represents phenylalkyl may be obtained by action of a phenylalkylmagnesium halide, such as a phenylalkylmagnesium bromide, on a compound of formula (III) in which $R_1$ represents 4-phenyl-1,2,3,6-tetrahydro-1-pyridyl or 4-(4-fluorophenyl)-1,2,3,6-tetrahydro-1-pyridyl.

This reaction is generally carried out in an inert organic solvent such as tetrahydrofuran or diethyl ether at a temperature close to 20° C.

The compounds of formula (I) in which $R_2$ represents a $-NR_4R_5$ radical in which $R_4$ represents hydrogen or alkyl and $R_5$ represents alkyl, phenyl, monohalogenated phenyl or pyridyl, and $R_1$, $R_3$ are as previously defined may be prepared by reaction of an amine of formula:

$$HNR_4R_5 \quad (XII)$$

in which $R_4$ and $R_5$ have the previously mentioned meanings with a compound of formula (II) in which $R_1$ represents 4-phenyl-1,2,3,6-tetrahydro-1-pyridyl or 4-(4-fluorophenyl)-1,2,3,6-tetrahydro-1-pyridyl.

This reaction is generally carried out in an inert aromatic solvent such as xylene, in the presence of p.toluenesulphonic acid at the boiling point of the solvent.

The compounds of formula (I) in which $R_2$ represents a $-NR_4R_5$ radical in which $R_4$ and $R_5$ have the previously mentioned meanings may also be prepared by reaction of a compound of formula:

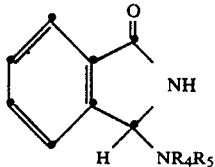

(XIII)

in which $R_4$ and $R_5$ have the same meanings as in formula (I) with a compound of formula:

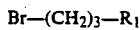

Br—$(CH_2)_3$—$R_1$ (XIV)

in which R has the same meanings as in formula (I).

This reaction is generally carried out in the presence of an alkaline metal hydride such as sodium hydride in an inert organic solvent such as dimethylformamide at a temperature close to 20° C.

The compounds of formula (XIII) may be obtained by action of 2-cyanobenzaldehyde on an amine $HNR_4R_5$ in which $R_4$ and $R_5$ have the same meanings as in formula (I).

This reaction is generally carried out in an inert organic solvent such as an alcohol (methanol, ethanol) at a temperature from 20° C. to the boiling point of the solvent.

The compounds of formula (XIV) may be obtained by bromination of alcohols of formula:

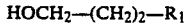

$HOCH_2$—$(CH_2)_2$—$R_1$ (XV)

in which $R_1$ has the same meanings as in formula (XIV).

This bromination is generally carried out with a brominating agent such as phosphorus tribromide in an inert organic solvent such as toluene at a temperature varying from 20° C. to the boiling point of the solvent.

The compounds of formula (XV) may be obtained by action of 3-bromopropanol on an amine of formula (IV) or (V).

This reaction is generally carried out in an inert organic solvent such as toluene in the presence of an acid acceptor such as a trialkylamine, e.g. triethylamine, at a temperature from 20° C. to the boiling point of the solvent.

The reaction mixtures obtained by the various processes previously described may be treated by conventional physical methods (e.g. evaporation, extraction, distillation, crystallization, or chromatography) or chemical methods, should the case arise (e.g. salt formation and regeneration of the base or the acid) so as to isolate the compounds of formula (I) in the pure state.

The compounds of formula (I), in the form of free bases, may, if desired, be converted into addition salts with an inorganic or organic acid by the action of such an acid in an organic solvent such as an alcohol, a ketone, an ether or a chlorinated solvent.

The compounds of formula (I) and their salts exhibit advantageous pharmacological properties. These compounds possess serotonin antagonist properties (at $5HT_2$ receptors) and are consequently useful for the treatment of diseases in which serotonin is involved and particularly diseases of the central nervous system, and the cardiovascular system and gastrointestinal disorders. These compounds are, in particular, useful for the treatment of anxiety, sleep disorders, depression, psychoses, especially schizophrenia, migraine, asthma, hypertension and urticaria, as analgesics, and as inhibitors of platelet aggregation.

The affinity of the compounds of formula (I) for the serotonin (type $S_2$) central receptor sites has been determined using a method based on that of J. E. LEYSEN et al., Mol. Pharmacol., 21, 301 (1982) which consists in measuring the affinity of the products under test for the bonding sites of tritiated ketanserine. In this test, the $IC_{50}$ of compounds of formula (I) is below 10 nM.

In a method based on that of S. J. CORNE and R. W. PICKERING, Psychopharmacologia, 11, 65–78 (1967), compounds of formula (I) have also shown themselves to be antagonistic to mescaline-induced head-twitches in mice.

In this test, the $AD_{50}$ of compounds of formula (I) administered orally was below 5 mg/kg.

Moreover, compounds of formula (I) exhibit low toxicity. Their $LD_{50}$ is generally above 100 mg/kg when they are administered orally to mice in a single dose.

Compounds of formula (I) of particular interest are those in which:

either $R_1$ represents 4-phenyl-1,2,3,6-tetrahydro-1-pyridyl or 4-(4-fluorophenyl)-1,2,3,6-tetrahydro-1-pyridyl, $R_2$ represents alkoxy, hydroxyl, alkyl, alkylthio or alkylcarbonyloxy and $R_3$ represents hydrogen or $R_1$ represents 4-(4-fluorophenyl)-1-piperazinyl, $R_2$ represents alkoxy and $R_3$ represents hydrogen; it being understood that when $R_1$ represents 4-phenyl-1,2,3,6-tetrahydro-1-pyridyl, $R_2$ is not hydroxyl.

Among these compounds, the more specially active are those compounds of formula (I) in which $R_2$ represents alkoxy.

The following compounds are especially remarkable:
3-methoxy-2-[3-(4-(4-fluorophenyl)-1,2,3,6-tetrahydro-1-pyridyl)propyl]-1-isoindolinone
3-methoxy-2-[3-(4-(4-fluorophenyl)-1-piperazinyl)-propyl]-1-isoindolinone
3-methoxy-2-[3-(4-phenyl-1,2,3,6-tetrahydro-1-pyridyl)propyl]-1-isoindolinone
3-ethoxy-2-[3-(4-phenyl-1,2,3,6-tetrahydro-1-pyridyl)-propyl]-1-isoindolinone
3-methylthio-2-[3-(4-phenyl-1,2,3,6-tetrahydro-1-pyridyl)propyl]-1-isoindolinone
3-methyl-2[3-(4-phenyl-1,2,3,6-tetrahydro-1-pyridyl)-propyl]-1-isoindolinone
3-acetoxy-2-[3-(4-phenyl-1,2,3,6-tetrahydro-1-pyridyl)-propyl]-1-isoindolinone
3-hydroxy-2-[3-(4-(4-fluorophenyl)-1,2,3,6-tetrahydro-1-pyridyl)propyl]-1-isoindolinone.

For medicinal purposes, the compounds of formula (I) may be used as such or as pharmaceutically acceptable acid addition salts, i.e. salts that are not toxic in the doses in which they are used.

As examples of pharmaceutically acceptable salts, may be cited addition salts formed with inorganic acids such as the hydrochloride, sulphate, nitrate or phosphate, or with organic acids, such as the acetate, propionate, oxalate, succinate, benzoate, fumarate, maleate, methanesulphonate, isethionate, theophyllineacetate, salicylate, phenolphthalinate, or methylene-bis-β- oxynaphthoate or substitution derivatives of these compounds.

The following Examples illustrate the invention.

EXAMPLE 1

A solution of 4-(4-fluorophenyl)-1,2,3,6-tetrahydropyridine (12.3 g) in toluene (20 cc) is added to a solution of 2-(3-bromopropyl)-3-hydroxy-1-isoindolinone (18.9 g) in toluene (200 cc), at a temperature close to 20° C. and in the course of 10 minutes, followed by a solution of triethylamine (9.8 cc) in toluene (20 cc). The mixture is agitated at a temperature close to 111° C. for 3 hours. After cooling to a temperature close to 20° C, the precipitate formed is separated by filtration and washed with toluene (3×50 cc). The organic phases are combined and concentrated to dryness under reduced pressure (20 mm Hg; 2.7 kPa) at 60° C. The residue obtained is dissolved in methylene chloride (50 cc) and the solution poured onto silica (1 kg) contained in a column of 8 cm diameter. Elution is carried out with a mixture of methylene chloride and methanol (98-2 by volume). The first 4000 cc are eliminated and the next 4000 cc are concentrated to dryness under reduced pressure (20 mm Hg; 2.7 kPa) at 40° C. The oil obtained is dissolved in methyl ethyl ketone (70 cc). A solution of oxalic acid (1.6 g) in methyl ethyl ketone (20 cc) is added, and agitation is maintained for about 1 hour. The precipitate formed is separated by filtration, washed with methyl ethyl ketone (20 cc), and then recrystallized from a boiling mixture of isopropanol and isopropyl ether (75-25 by volume,150 cc). 4.8 g of 3-hydroxy-2-[3-(4-(4-fluorophenyl)-1,2,3,6-tetrahydro-1-pyridyl)-propyl]-1-isoindolinone oxalate are obtained, melting at 93° C.

2-(3-Bromopropyl)-3-hydroxy-1-isoindolinone may be prepared in the following way: potassium borohydride (21.6 g) is added to a solution of 2-(3-bromopropyl)phthalimide (53.6 g) in methanol (450 cc) at a temperature close to 20° C. and agitation is continued for 24 hours. The resulting solution is poured into distilled water (1000 cc) and extracted with ethyl acetate (4×150 cc). The organic extracts are combined, dried over anhydrous magnesium sulphate and concentrated to dryness under reduced pressure (20 mm Hg; 2.7 kPa) at 40° C. The residue obtained is dissolved in methylene chloride (100 cc) and the solution poured onto silica (750 g) contained in a column of 8 cm diameter. Elution is carried out with methylene chloride (2 liters), then a mixture of methylene chloride and methanol (99-1 by volume, 1 liter), then a mixture of methylene chloride and methanol (98-2 by volume, 1 liter), and then a mixture of methylene chloride and methanol (97-3 by volume, 1 liter). The corresponding eluates are eliminated. Elution is then carried out with a mixture of methylene chloride and methanol (97-3 by volume, 3 liters) and the corresponding eluate is concentrated to dryness under reduced pressure (20 mm Hg; 2.7 kPa) at 50° C. 18.9 g of a white oil are obtained, whose Rf on a silica plate and in a mixture of methylene chloride and methanol (95-5 by volume) is 0.39.

2-(3-bromopropyl)phthalimide may be prepared according to the method described by T. O. SOINE and BUCHDAHL, Organic Synthesis, 32, 18 (1952).

EXAMPLE 2

28.5 cc of concentrated sulphuric acid is added to an agitated solution of 2-[3-(4-(4-fluorophenyl)-1,2,3,6-tetrahydro-1-pyridyl)propyl]-3-hydroxy-1-isoindolinone (5.7 g) in methanol (145 cc) at a temperature close to 20° C. in the course of 10 minutes. Agitation is continued for 5 hours at a temperature close to 65° C. After cooling the solution to a temperature close to 0° C., 70 cc of a 33% aqueous solution of ammonia is added in the course of 1 hour. The precipitate formed is filtered and washed with methanol (50 cc). The filtrate is diluted with distilled water (200 cc) and a 33% aqueous solution of ammonia (50 cc) and extracted with methylene chloride (3×200 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (10 cc) and the solution poured onto silica (550 g) contained in a column of 8 cm diameter. Elution is carried out with a mixture of methylene chloride and methanol (90-10 by volume). The first 900 cc are eliminated and the following 200 cc are evaporated to dryness under reduced pressure (20 mm Hg; 2.7 kPa) at 50° C. The residue obtained is dissolved in methyl ethyl ketone (10 cc). A solution of oxalic acid (0.6 g) in methyl ethyl ketone (5 cc) is added and agitation continued for 1 hour at a temperature close to 20° C. The precipitate formed is separated by filtration. 2.4 g of 3-methoxy-2-[3-(4-(4-fluorophenyl)-1,2,3,6-tetrahydro-1-pyridyl)propyl]-1-isoindolinone oxalate are obtained, melting at 139° C.

EXAMPLE 3

A solution of 2-[3-(4-phenyl-1,2,3,6-tetrahydro-1pyridyl)propyl]-3-hydroxy-1-isoindolinone (5.2 g) in anhydrous dimethyl formamide (50 cc) is added to a suspension of sodium hydride (as a 50% suspension in oil, 0.8 g) in anhydrous dimethylformamide (10 cc) at a temperature close to 20° C. in the course of 15 minutes, and agitation is continued for 2 hours. Then, 1 cc of methyl iodide is added in the course of 5 minutes and agitation is continued for a further 20 hours. The suspension obtained is poured into distilled water (1000 cc) and extracted with methylene chloride (3×1000 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (20 cc) and the solution poured onto silica (300 g) contained in a column of 7 cm diameter. Elution is carried out with a mixture of methylene chloride and methanol (98-2 by volume, 1 liter) and the corresponding eluate evaporated to dryness under reduced pressure (20 mm Hg; 2.7 kPa) at 50° C. The residue obtained is dissolved in methyl ethyl ketone (30 cc). A solution of oxalic acid (0.7 g) in methyl ethyl ketone (10 cc) is added and agitation is continued for 1 hour at a temperature close to 20° C. The precipitate formed is separated by filtration. 2.6 g of 3-methoxy-2-[3-(4-phenyl-1,2,3,6-tetrahydro-1-pyridyl)propyl]-1-isoindolinone oxalate are thus obtained, melting at 160° C.

2-[3-(4-Phenyl-1,2,3,6-tetrahydro-1-pyridyl)propyl]3-hydroxy-1-isoindolinone can be obtained in the following manner: potassium borohydride (3.24 g) is added to a solution of 2-[3-(4-phenyl-1,2,3,6-tetrahydro-1-pyridyl)propyl]phthalimide (21 g) in methanol (210 cc), at a temperature close to 20° C. and agitation is continued for 24 hours. More potassium borohydride (1.62 g) is added and agitation continued for a further 6 hours. The solution obtained is subsequently poured into distilled water (1000 cc) and extracted with ethyl acetate (4×150 cc). The organic extracts are combined, dried over anhydrous magnesium sulphate, filtered and concentrated to dryness under reduced pressure (20 mm Hg; 2.7 kPa) at 40° C. The residue obtained is dissolved in acetonitrile (150 cc). A solution of oxalic acid (5.4 g) in acetonitrile (200 cc) is added, and agitation is continued for 1 hour at a temperature close to 20° C. The precipitate formed is separated by filtration, then recrystallized from boiling acetonitrile (700 cc). 10.2 g of 2-[3-(4-phenyl-1,2,3,6-tetrahydro-1-pyridyl)propyl]-3-hydroxy-1-isoindolinone oxalate are obtained, melting at 130-135° C.

2-[3-(4-Phenyl-1,2,3,6-tetrahydro-1-pyridyl)-propyl]phthalimide may be prepared in the following manner: 7.4 cc of triethylamine is added to an agitated solution of 2-(3-bromopropyl)phthalimide (16.1 g) and 4-phenyl-1,2,3,6-tetrahydropyridine (10.4 g) in toluene (160 ml) in the course of 10 minutes and at a temperature close to 20° C. Agitation is continued for 6 hours at a temperature close to 111° C. After cooling to a temperature close to 20° C., the precipitate formed is separated by filtration and washed with toluene (30 cc). The organic phases are combined and concentrated to dryness under reduced pressure (20 mm Hg; 2.7 kPa) at 60° C. The precipitate obtained is recrystallized from boiling isopropanol (65 cc) 21 g of 2-[3-(4-phenyl-1,2,3,6-tetrahydro-1-pyridyl)-propyl]phthalimide are thus obtained, melting at 90° C.

2-(3-Bromopropyl)phthalimide may be prepared following the method described by T. O. SOINE and BUCHDAHL, Organic Synthesis, 32, 18 (1952).

EXAMPLE 4

The same procedure is followed as in Example 2, starting from an agitated solution of 2-[3-(4-(4-fluorophenyl)-1-piperazinyl)propyl]-3-hydroxy-1-isoindolinone (6.8 g) in methanol (170 cc) to which 33.5 cc of concentrated sulphuric acid is added at a temperature close to 20° C. in the course of 15 minutes. Agitation is continued for 5 hours at a temperature close to 65° C. After cooling the solution to a temperature close to 0° C., 83 cc of a 33% aqueous solution of ammonia is added in the course of 1 hour. The precipitate formed is filtered and washed with methanol (50 cc). The filtrate is diluted with distilled water (200 cc) and a 33% aqueous solution of ammonia (50 cc) and extracted with methylene chloride (3×200 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (20 cc) and the solution is poured onto silica (500 g) contained in a column of 8 cm diameter. Elution is carried out with a mixture of methylene chloride and methanol (99-1 by volume). The first 300 cc are eliminated and the next 3500 cc are evaporated to dryness under reduced pressure (20 mm Hg; 2.7 kPa) at 50° C. The residue obtained is dissolved in acetonitrile (50 cc). A solution of oxalic acid (1.1 g) in acetonitrile (25 cc) is added and agitation continued for 1 hour at a temperature close to 20° C. The precipitate formed is separated by filtration. 4.1 g of 3-methoxy-2-[3-(4-(4-fluorophenyl)-1-piperazinyl)propyl]-1-isoindolinone oxalate are thus obtained, melting at 177° C.

2-[3-(4-(4-Fluorophenyl)-1-piperazinyl)propyl]-3-hydroxy-1-isoindolinone may be prepared as described in Example 3 for the preparation of 2-[3-(4-phenyl-1,2,3,6-tetrahydro-1-pyridyl)propyl]-3-hydroxy-1-isoindolinone, but starting from an agitated solution of 2-[3-(4-(4-fluorophenyl)-1-piperazinyl)propyl]phthalimide (10.3 g) in methanol (200 cc) and distilled water (10 cc) to which potassium borohydride (1.51 g) is added at a temperature close to 20° C. Agitation is continued for 24 hours. The solution obtained is poured into distilled water (130 cc) and extracted with methylene chloride (4×100 cc). The organic extracts are combined, dried over anhydrous magnesium sulphate, filtered and concentrated to dryness under reduced pressure (20 mm Hg; 2.7 kPa) at 40° C. The residue obtained is dissolved in boiling acetonitrile (125 cc). After cooling to a temperature close to 20° C., the precipitate formed is separated by filtration. 6.9 g of 2-[3-(4-(4-fluorophenyl)-1-piperazinyl)propyl]-3-hydroxy-1-isoindolinone are thus obtained, melting at 155° C.

2-[3-(4-(4-Fluorophenyl)-1-piperazinyl)propyl]phthalimide may be prepared as described in Example 3 for the preparation of 2-[3-(4-phenyl-1,2,3,6-tetrahydro-1-pyridyl)propyl]phthalimide, but starting from an agitated solution of 2-(3-bromopropyl)phthalimide (15 g) and 4-(4-fluorophenyl)piperazine (10.1 g) in toluene (500 cc) to which 7,8 cc of triethylamine is added in the course of 10 minutes at a temperature close to 20° C. The precipitate obtained is dissolved in methylene chloride (50 cc) and poured onto silica (1250 g) contained in a column of 8 cm diameter. Elution is carried out with a mixture of methylene chloride and methanol (98-2 by volume). The first 750 cc are eliminated and the eluates corresponding to the next 2250 cc are concentrated to dryness under reduced pressure (20 mm Hg; 2.7 kPa) at 50° C. 13.3 g are obtained of an orangey oil whose Rf on a silica plate and in a mixture of methylene chloride and methanol (95-5 by volume) is 0.5.

EXAMPLE 5

The same procedure is followed as in Example 2, but starting from an agitated solution of 2-[3-(4-(4-chlorophenyl)-1-piperazinyl)propyl-3-hydroxy-1-isoindolinone (4.8 g) in methanol (115 cc) to which 22.6 cc of concentrated sulphuric acid is added at a temperature close to 20° C. and in the course of 10 minutes. Agitation is continued for 5 hours at a temperature close to 65° C. After cooling the solution to a temperature close to 0° C., 55 cc of a 33% aqueous solution of ammonia is added in the course of 1 hour. The precipitate formed is filtered and washed with methanol (50 cc). The filtrate is diluted with distilled water (200 cc) and 33% aqueous solution of ammonia (50cc), and extracted with methylene chloride (3×200 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (20 cc) and the solution is poured onto silica (500 g) contained in a column of 8 cm diameter. Elution is carried out with a mixture of methylene chloride and methanol (98.5-1.5 by volume). The first 100 cc are eliminated and the next 630 cc are evaporated to dryness under reduced pressure (20 mm Hg; 2.7 kPa) at 50° C. The residue obtained is dissolved in acetonitrile (30 cc). A solution of oxalic acid (0.63 g) in acetonitrile (15 cc) is added and agitation is continued for 1 hour at a temperature close to 20° C. The precipitate formed is separated by filtration. 2.9 g of 3-methoxy-2-[3-(4-(4-chlorophenyl)-1-piperazinyl)-propyl]-1-isoindolinone oxalate are thus obtained, melting at 200° C.

2-[3-(4-(4-Chlorophenyl)-1-piperazinyl)propyl]-3-hydroxy-1-isoindolinone may be prepared as described in Example 3 for the preparation of 2-[3-(4-phenyl-1,2,3,6-tetrahydro-1-pyridyl)propyl]-3-hydroxy-1-isoindolinone, but starting from an agitated solution of 2-[3-(4-(4-chlorophenyl)-1-piperazinyl)propyl]phthalimide (4 g) in methanol (120 cc) and distilled water (10 cc) to which potassium borohydride (0.56 g) is added at a temperature close to 20° C. Agitation is continued for 24 hours. The solution obtained is poured into distilled water (50 cc) and extracted with methylene chloride (4×50 cc). The organic extracts are combined, dried over anhydrous magnesium sulphate, filtered and concentrated to dryness under reduced pressure (20 mm Hg; 2.7 kPa) at 40° C. The residue obtained is dissolved in boiling acetonitrile (30 cc). After cooling to a temperature close to 20° C., the precipitate formed is separated by filtration. 2.4 g of 2-[3-(4-(4-chlorophenyl)-1-piperazinyl)propyl]-3-hydroxy-1-isoindolinone are obtained, melting at 173° C.

2-[3-(4-(4-Chlorophenyl)-1-piperazinyl)propyl]phthalimide may be prepared as described in Example 3 for the preparation of 2-[3-(4-phenyl-1,2,3,6-tetrahydro-1-pyridyl)propyl]-3-hydroxy-1-isoindolinone, but starting from an agitated solution of 2-(3-bromopropyl)phthalimide (5.3 g) and 4-(4-chlorophenyl)piperazine (5.4 g) in toluene (100 cc) to which 2.8 cc of triethylamine is added in the course of 5 minutes and at a temperature close to 20° C. The precipitate obtained is dissolved in methylene chloride (20 cc) then poured onto silica (200 g) contained in a column of 4 cm diameter. Elution is carried out with a mixture of methylene chloride and methanol (98-2 by volume). The first 300 cc are eliminated and the eluates corresponding to the next 400 cc are concentrated to dryness under reduced pressure (20 mm Hg; 2.7 kPa) at 50° C. 4 g of 2-[3-(4-(4-chlorophenyl)-1-piperazinyl)propyl]phthalimide are thus obtained, melting at 120° C.

EXAMPLE 6

The same procedure is followed as in Example 2, but starting from an agitated solution of 2-[3-(4-phenyl-1,2,3,6-tetrahydro-1-pyridyl)propyl]-3-hydroxy-1-isoindolinone (7 g) in ethanol (265 cc) to which 37 cc of concentrated sulphuric acid is added at a temperature close to 20° C. and in the course of 15 minutes. Agitation is continued for 4 hours at a temperature close to 65° C. After cooling the solution to a temperature close to 0° C., 90 cc of a 33% aqueous solution of ammonia is added in the course of 1 hour. The precipitate formed is filtered and washed with methanol (50 cc). The filtrate is diluted with distilled water (200 cc) and a 33% aqueous solution of ammonia (70 cc) and extracted with methylene chloride (3×250 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (30 cc) and poured onto silica (500 g) contained in a column of 8 cm diameter. Elution is carried out with a mixture of methylene chloride and methanol (95-5 by volume). The first 1000 cc are eliminated, the next 900 cc are evaporated to dryness under reduced pressure (20 mm Hg; 2.7 kPa) at 50° C. The residue obtained is dissolved in methyl ethyl ketone (50 cc). A solution of oxalic acid (1.2 g) in methyl ethyl ketone (20 cc) is added and agitation is continued for 1 hour at a temperature close to 20° C. The precipitate formed is separated by filtration. 4.9 g of 3-ethoxy-2-[3-(4-phenyl-1,2,3,6-tetrahydro-1-pyridyl)propyl]-1-isoindolinone oxalate are thus obtained, melting at 150° C.

EXAMPLE 7

Para-toluenesulphonic acid (50 mg) is added to an agitated solution of 2-[3-(4-phenyl-1,2,3,6-tetrahydro-1-pyridyl)propyl]-3-hydroxy-1-isoindolinone (5 g) and aniline (1.7 g) in xylene (100 cc) at a temperature close to 20° C. in a Dean Stark apparatus. Agitation is continued for 9 hours at a temperature close to 135° C. After cooling to a temperature close to 20° C., the solution is washed with aqueous sodium bicarbonate solution (2×50 cc) then with distilled water (2×30 cc). The organic extracts are combined, dried over anhydrous magnesium sulphate, filtered and concentrated to dryness under reduced pressure (20 mm Hg; 2.7 kPa) at 80° C. The residue obtained is dissolved in methylene chloride (10 cc) and poured onto silica (100 g) contained in a column of 2 cm diameter. Elution is carried out with a mixture of methylene chloride and methanol (95-5 by volume) (1300 cc) and the corresponding eluate is concentrated to dryness under reduced pressure (20 mm Hg; 2.7 kPa). The precipitate formed is recrystallized from boiling acetonitrile (30 cc). 5.7 g of 3-phenylamino-2-[3-(4-phenyl-1,2,3,6-tetrahydro-1-pyridyl)propyl]-1-isoindolinone are obtained, melting at 119° C.

EXAMPLE 8

Para-toluenesulphonic acid (50 mg) is added to an agitated solution of 2-[3-(4-phenyl-1,2,3,6-tetrahydro-1-pyridyl)propyl]-3-hydroxy-1-isoindolinone (10 g) and 4-chlorophenylamine (4.6 g) in xylene (230 cc) at a temperature close to 20° C. in a Dean Stark apparatus. Agitation is continued for 6 hours at a temperature close to 135° C. After cooling to a temperature close to 20° C., the precipitate formed is filtered, washed with xylene (2×50 cc), dried under reduced pressure (20 mm Hg; 2.7 kPa) and recrystallized from boiling acetonitrile (360 cc). 7.1 g of 3-(4-chlorophenylamino)-2-[3-(4-phenyl-1,2,3,6-tetrahydro-1-pyridyl)propyl]-1-isoindolinone are obtained, melting at 188° C.

EXAMPLE 9

Para-toluenesulphonic acid (50 mg) is added to an agitated solution of 2-[3-(4-phenyl-1,2,3,6-tetrahydro-1-pyridyl)propyl]-3-hydroxy1-isoindolinone (6 g) and 2-aminopyridine (2 g) in xylene (150 cc) at a temperature close to 20° C. in a Dean Stark apparatus. Agitation is continued for 5 hours at a temperature close to 135° C. After cooling to a temperature close to 20° C., the solution is washed with aqueous sodium bicarbonate solution (2×100 cc) then with distilled water (2×50 cc). The organic extracts are combined, dried over anhydrous magnesium sulphate, filtered and concentrated to dryness under reduced pressure (20 mm Hg; 2.7 kPa) at 80° C. The precipitate is recrystallized from boiling acetonitrile (45 cc). 3.7 g of 3-(2-pyridylamino)-2-[3-(4-phenyl-1,2,3,6-tetrahydro-1-pyridyl)propyl]-1-isoindolinone are obtained, melting at 153° C.

EXAMPLE 10

A solution of 3-(N-methyl-N-phenylamino)-1-isoindolinone (10 g) in anhydrous dimethylformamide (200 cc) is added to a suspension of sodium hydride (as a 50% suspension in oil) (2.2 g) in anhydrous dimethylformamide (200 cc) at a temperature close to 20° C. in the course of 30 minutes and agitation is continued for 1 hour. Then, a solution of 3-(4-phenyl-1,2,3,6-tetrahydro-1-pyridyl)-1-bromopropane (13 g) in dimethylformamide (100 cc) is added in the course of 15 minutes, and agitation is continued for a further 20 hours. The solution obtained is evaporated to dryness under reduced pressure (1 mm Hg; 0.1 kPa). The residue obtained is dissolved in methylene chloride (200 cc) and washed with distilled water (3×50 cc). The organic extracts are dried over anhydrous magnesium sulphate, filtered and concentrated to dryness under reduced pressure (20 mm Hg; 2.7.kPa) at 40° C. The residue obtained is dissolved in methylene chloride (40 cc) then poured onto silica (800 g) contained in a column of 8 cm diameter. Elution is carried out with a mixture of methylene chloride and methanol (95-5 by volume). The first 2300 cc are eliminated and the next 1100 cc are concentrated to dryness under reduced pressure (20 mm Hg; 2.7 kPa). The residue obtained is dissolved in methyl ethyl ketone (50 cc). A solution of oxalic acid (1.1 g) in methyl ethyl ketone (15 cc) is added, and agitation continued for 1 hour at a temperature close to 20° C. The precipitate formed is separated by filtration. 5.4 g of 3-(N-methyl-N-phenylamino)-2-[3-(4-phenyl-1,2,3,6-tetrahydro-1-pyridyl)propyl]-1-isoindolinone oxalate are obtained, melting at 159° C.

3-(N-methyl-N-phenylamino)-1-isoindolinone may be prepared in the following manner: 65 g of N-methyl-N-phenylamine are added to a solution of 2-cyanobenzaldehyde (26 g) in methanol (280 cc) in the course of 10 minutes at a temperature close to 20° C. The reaction mixture is heated to a temperature close to 40° C. for 24 hours. After cooling to a temperature close to 20° C., the solution is concentrated to dryness under reduced pressure (20 mm Hg; 2.7 kPa) at 50° C. The residue obtained is dissolved in methylene chloride (50 cc) and poured onto silica (600 cc) contained in a column of diameter 8 cm. Elution is carried out with a mixture of methylene chloride and methanol (98-2 by volume). The first 2000 cc are eliminated and the eluate corresponding to the next 2000 cc is concentrated to dryness under reduced pressure (20 mm Hg; 2.7 kPa). A brown oil is obtained whose Rf on a silica plate and in a mixture of methylene chloride and methanol (97-3 by volume) is 0.4.

3-(4-Phenyl-1,2,3,6-tetrahydro-1-pyridyl)-1-bromopropane may be prepared in the following manner: 2.7 cc of phosphorus tribromide is added to a vigorously agitated solution of 3-(4-phenyl-1,2,3,6-tetrahydro-1-pyridyl)-1-propanol (8.7 g) in toluene (100 cc) in the course of 5 minutes and at a temperature close to 20° C. The suspension is heated to a temperature close to 111° C. for 2 hours. After cooling to a temperature close to 20° C., the suspension is filtered, the precipitate obtained is dissolved in methylene chloride (250 cc). The organic phase is washed with distilled water (150 cc), dried over anhydrous magnesium sulphate then concentrated to dryness under reduced pressure (20 mm Hg; 2.7 kPa). 14 g of 3-(4-phenyl--1,2,3,6-tetrahydro-1-pyridyl)1-bromopropane hydrobromide are obtained, melting at 185° C.

3-(4-Phenyl-1,2,3,6-tetrahydro-1-pyridyl)-1-propanol may be prepared in the following manner: 36.7 cc of triethylamine is added to a solution of 3-bromo-1-propanol (25 cc) and 4-phenyl-1,2,3,6-tetrahydro-pyridine (42 g) in toluene (500 cc) in the course of 10 minutes and at a temperature close to 20° C. The solution is heated to a temperature close to 111° C. for 16 hours. After cooling to a temperature close to 20° C., the suspension is filtered, the precipitate is washed with toluene (2×50 cc). The combined organic extracts are treated with animal charcoal and evaporated to dryness under reduced pressure (20 mm Hg; 2.7 kPa) at 60° C. 42 g of a yellow oil are thus obtained whose Rf on a silica plate and in a mixture of methylene chloride and methanol (90-10 by volume) is 0.25.

EXAMPLE 11

A solution of 3-dimethylamino-1-isoindolinone (11.7 g) in anhydrous dimethylformamide (300 cc) is added to a suspension of sodium hydride (as a 50% suspension in oil) (3.5 g) in anhydrous dimethylformamide (150 cc) at a temperature close to 20° C. in the course of 30 minutes, and agitation is continued for 1 hour. Then, a solution of 3-(4-phenyl-1,2,3,6-tetrahydro-1-pyridyl)-1-bromopropane (20.5 g) in dimethylformamide (150 cc) is added in the course of 15 minutes, and agitation is continued for a further 20 hours. The solution obtained is evaporated to dryness under reduced pressure (1 mm mercury; 0.1 kPa). The residue obtained is dissolved in methylene chloride (350 cc) and washed with distilled water (3×150 cc). The organic extract is dried over anhydrous magnesium sulphate, filtered and concentrated to dryness under reduced pressure (20 mm Hg; 2.7 kPa) at 40° C. The residue obtained is dissolved in methylene chloride (50 cc) and poured onto silica (1000 g) contained in a column of 8 cm diameter. Elution is carried out with a mixture of methylene chloride and methanol (95-5 by volume). The first 2300 cc are eliminated and the eluate corresponding to the next 1500 cc is concentrated to dryness under reduced pressure (20 mm Hg; 2.7 kPa). The residue obtained is dissolved in methyl ethyl ketone (80 cc). A solution of oxalic acid (1.9 g) in methyl ethyl ketone (20 cc) is added and agitation is continued for 1 hour at a temperature close to 20° C. The precipitate formed is separated by filtration. 7.6 g of 3-dimethylamino-2-[3-(4-phenyl-1,2,3,6-tetrahydro-1-pyridyl)propyl]-1-isoindolinone oxalate are thus obtained, melting at 159° C.

3-Dimethylamino-1-isoindolinone may be prepared in the following manner: 60 cc of dimethylamine is added to a solution of 2-cyanobenzaldehyde (40 g) in methanol (450 cc) in the course of 10 minutes at a temperature close to 20° C. The reaction mixture is heated to a temperature close to 40° C. for 24 hours. After cooling to a temperature close to 20° C., the solution is concentrated to dryness under reduced pressure (20 mm Hg; 2.7 kPa) at 50° C. The residue obtained is dissolved in boiling acetonitrile (300 cc), treated with animal charcoal and filtered hot. After cooling to a temperature close to 20° C., the precipitate formed is filtered. 10.1 g of 3-dimethylamino-1-isoindolinone are thus obtained, whose Rf on a silica plate and in a mixture of methylene chloride and methanol (90-10 by volume) is 0.35.

EXAMPLE 12

A solution of 3-methylamino-1-isoindolinone (6.8 g) in anhydrous dimethylformamide (200 cc) is added to a suspension of sodium hydride (as a 50% suspension in oil) (2.2 g) in anhydrous dimethylformamide (100 cc) at a temperature close to 20° C. in the course of 15 minutes and agitation is continued for 1 hour. Then, a solution of 3-(4-phenyl-1,2,3,6-tetrahydro-1-pyridyl)-1-bromopropane (13 g) in dimethylformamide (100 cc) is added in the course of 10 minutes, and agitation is continued for a further 20 hours. The solution obtained is evaporated to dryness under reduced pressure (1 mm Hg; 0.1 kPa).

The residue obtained is dissolved in methylene chloride (500 cc) and washed with distilled water (3×500 cc). The organic phase is dried over anhydrous magnesium sulphate, filtered and concentrated to dryness under reduced pressure (20 mm Hg; 2.7 kPa) at 40° C. The residue obtained is dissolved in methylene chloride (20 cc) and poured onto silica (750 g) contained in a column of 8 cm diameter. Elution is carried out with a mixture of methylene chloride and methanol (92-8 by volume). The first 3750 cc are eliminated and the eluate corresponding to the next 600 cc is concentrated to dryness under reduced pressure (20 mm Hg; 2.7 kPa). The residue obtained is dissolved in methyl ethyl ketone (50 cc). A solution of oxalic acid (1.2 g) in methyl ethyl ketone (20 cc) is added and agitation continued for 1 hour at a temperature close to 20° C. The precipitate formed is separated by filtration. 5 g of 3-methylamino-2-[3-(4-phenyl-1,2,3,6-tetrahydro-1-pyridyl)propyl]-1-isoindolinone oxalate are thus obtained, melting at 122° C.

3-Methylamino-1-isoindolinone may be prepared in the following manner: 18.6 g of dimethylamine is added to a solution of 2-cyanobenzaldehyde (26 g) in methanol (300 cc) in the course of 10 minutes and at a temperature lose to −70° C. in an autoclave. The reaction mixture is then heated to a temperature close to 40° C. for 24 hours. After cooling to a temperature close to 20° C., the solution is concentrated to dryness under reduced pressure (20 mm Hg; 2.7 kPa) at 50° C. The precipitate obtained is recrystallized from boiling acetonitrile (150 cc). 20.9 g of 3-methylamino-1-isoindolinone are thus obtained, melting at 152° C.

EXAMPLE 13

A solution of 2-[3-(4-phenyl-1,2,3,6-tetrahydro-1pyridyl)propyl]-3-hydroxy-1-isoindolinone (8 g) in anhydrous dimethylformamide (75 cc) is added to a suspension of sodium hydride (as a 50% suspension in oil) (1.2 g) in anhydrous dimethylformamide (15 cc) at a temperature close to 20° C. in the course of 15 minutes and agitation is continued for 3 hours. Then, 2.6 g of butyryl chloride is added in the course of 10 minutes, and agitation is continued for a further 20 hours. The suspension obtained is poured into distilled water (400 cc) and extracted with methylene chloride (4×200 cc). The organic extracts are combined, dried over anhydrous magnesium sulphate, filtered and concentrated to dryness under reduced pressure (20 mm Hg; 2.7 kPa) at 40° C. The residue obtained is dissolved in acetonitrile (120 cc). A solution of oxalic acid (2.3 g) in acetonitrile (60 cc) is added and agitation continued for 1 hour at a temperature close to 20° C. The precipitate formed is separated by filtration. 8.1 g of 3-butyryloxy-2-[3-(4-phenyl-1,2,3,6-tetrahydro-1-pyridyl)propyl]-1-isoindolinone oxalate are thus obtained, melting at 160° C.

EXAMPLE 14

A solution of 2-[3-(4-phenyl-1,2,3,6-tetrahydro-1-pyridyl)propyl]-3-hydroxy-1-isoindolinone (6 g) in anhydrous dimethylformamide (70 cc) is added to a suspension of sodium hydride (as a 50% suspension in oil) (0.8 g) in anhydrous dimethylformamide (20 cc) at a temperature close to 20° C. in the course of 10 minutes and agitation is continued for 1 and a half hours. Then, 1.4 g of acetyl chloride is added in the course of 10 minutes, and agitation is continued for a further 20 hours. The suspension obtained is poured into distilled water (70 cc) and extracted with methylene chloride (4×50 cc). The organic extracts are combined, dried over anhydrous magnesium sulphate, filtered and concentrated to dryness under reduced pressure (20 mm Hg; 2.7 kPa) at 40° C. The residue obtained is dissolved in methyl ethyl ketone (55 cc). A solution of oxalic acid (1.3 g) in methyl ethyl ketone (20 cc) is added and agitation continued for 1 hour at a temperature close to 20° C. The precipitate formed is separated by filtration. 1.8 g of 3-acetoxy-2-[3-(4-phenyl-1,2,3,6-tetrahydro-1-pyridyl)propyl]-1-isoindolinone oxalate are thus obtained, melting at 166° C.

EXAMPLE 15

15 A solution of 2-[3-(4-phenyl-1,2,3,6-tetrahydro-1pyridyl)propyl]-3-hydroxy-1-isoindolinone (7 g) in anhydrous dimethylformamide (75 cc) is added to a suspension of sodium hydride (as a 50% suspension in oil) (1 g) in anhydrous dimethylformamide (25 cc) at a temperature close to 20° C. in the course of 10 minutes and agitation is continued for 2 hours. Then, 2.3 g of isobutyryl chloride is added in the course of 5 minutes, and agitation is continued for a further 20 hours. The suspension obtained is poured into distilled water (100 cc) and extracted with methylene chloride (4×50 cc). The organic extracts are combined, dried over anhydrous magnesium sulphate, filtered and concentrated to dryness under reduced pressure (20 mm Hg; 2.7 kPa) at 40° C. The residue obtained is dissolved in methyl ethyl ketone (45 cc). A solution of oxalic acid (1.5 g) in methyl ethyl ketone (35 cc) is added and agitation continued for 1 hour at a temperature close to 20° C. The precipitate formed is separated by filtration and recrystallized from boiling methanol (200 cc). 3 g of 3-isobutyryloxy-2-[3-(4-phenyl-1,2,3,6-tetrahydro-1-pyridyl)propyl]-1-isoindolinone oxalate are thus obtained, melting at 164° C.

EXAMPLE 16

A solution of 2-[3-(4-phenyl-1,2,3,6-tetrahydro-1pyridyl)propyl]-3-hydroxy-1-isoindolinone (7 g) in anhydrous dimethylformamide (75 cc) is added to a suspension of sodium hydride (as a 50% suspension in oil) (1 g) in anhydrous dimethylformamide (25 cc) at a temperature close to 20° C. in the course of 10 minutes and agitation is continued for 2 hours. Then, 3.5 g of phenylacetyl chloride is added in the course of 5 minutes, and agitation is continued for a further 20 hours. The suspension obtained is poured into distilled water (100 cc) and extracted with methylene chloride (4×50 cc). The organic extracts are combined, dried over anhydrous magnesium sulphate, filtered and concentrated to dryness under reduced pressure (20 mm Hg; 2.7 kPa) at 40° C. The residue obtained is dissolved in methyl ethyl ketone (30 cc). A solution of oxalic acid (1.1 g) in methyl ethyl ketone (15 cc) is added and agitation continued for 1 hour at a temperature close to 20° C. The precipitate formed is separated by filtration. 4.2 g of 3-phenylacetoxy-2-[3-(4-phenyl-1,2,3,6-tetrahydro-1pyridyl)propyl]-1-isoindolinone oxalate are thus obtained, melting at 134° C.

EXAMPLE 17

An agitated solution of 2-[3-(4-phenyl-1,2,3,6-tetrahydro-1-pyridyl)propyl]-3-hydroxy-1-isoindolinone (11 g) in acetic acid (80 cc) is heated to a temperature close to 60° C. and 11.3 g of powdered zinc is added in small portions in the course of 10 minutes. The suspension obtained is then heated to a temperature close to 120° C.

for 5 hours. The suspension is evaporated to dryness under reduced pressure (20 mm Hg; 2.7 kPa) at 80° C. The residue is dissolved in distilled water (250 cc) and the solution is extracted with methylene chloride (4×50 cc). The organic extracts are combined, dried over anhydrous magnesium sulphate, filtered and concentrated to dryness under reduced pressure (20 mm Hg; 2.7 kPa) at 40° C. The precipitate formed is recrystallized from boiling acetonitrile (25 cc). 6.1 g of 2-[3-(4-phenyl-1,2,3,6-tetrahydro-1-pyridyl)propyl]-1-isoindolinone are thus obtained, melting at 104° C.

EXAMPLE 18

5 cc of methylmercaptan is added to a solution of methyl 2-formylbenzoate (3.6 g) and 3-(4-phenyl-1,2,3,6-tetrahydro-1-pyridyl)-1-aminopropane (9.6 g)in tetrahydrofuran (255 cc) in an autoclave, at a temperature close to −20° C. in the course of 5 minutes. The solution is heated to a temperature close to 60° C. for 4 hours. After cooling to a temperature close to 20° C., the solution is poured into 1N sodium hydroxide (300 cc) and washed with distilled water (3×500 cc). The organic extract is dried over anhydrous magnesium sulphate, filtered and concentrated to dryness under reduced pressure (20 mm Hg; 2.7 kPa) at 40° C. The residue obtained is dissolved in ethyl acetate (20 cc) and poured onto silica (750 g) contained in a column of 8 cm diameter. Elution is carried out with ethyl acetate. The first 3400 cc are eliminated and the next 3100 cc are evaporated to dryness under reduced pressure (20 mm Hg; 2.7 kPa) at 40° C. The residue obtained is dissolved in methyl ethyl ketone (70 cc). A solution of oxalic acid (1.7 g) in methyl ethyl ketone (20 cc) is added and agitation continued for 1 hour at a temperature close to 20° C. The precipitate formed is separated by filtration. 5.9 g of 3-methylthio-2-[3-(4-phenyl-1,2,3,6-tetrahydro-1-pyridyl)propyl]-1-isoindolinone oxalate are thus obtained, melting at 169° C.

3-(4-Phenyl-1,2,3,6-tetrahydro-1-pyridyl)- 1-aminopropane may be prepared in the following manner: 17.2 cc of hydrazine monohydrate is added to an agitated solution of 2-[3-(4-phenyl-1,2,3,6-tetrahydro-1-pyridyl)-propyl] phtalimide (41 g) in ethanol (355 cc) in the course of 20 minutes and at a temperature close to 20° C. The solution obtained is then heated to a temperature close to 78° C. for 4 and a half hours. After cooling to a temperature close to 0° C., concentrated hydrochloric acid (82 cc) is added to the suspension formed and agitation is continued at a temperature close to 20° C. for 16 hours. The precipitate formed is separated by filtration and washed with distilled water (3×50 cc). 1N sodium hydroxide (350 cc) is added to the combined aqueous and ethanolic phases, then the solution is extracted with methylene chloride (3×500 cc). The organic extracts are combined, dried over anhydrous magnesium sulphate, filtered and concentrated to dryness under reduced pressure (20 mm Hg; 2.7 kPa) at 40° C. The precipitate obtained is recrystallized from boiling isopropanol (65 cc). 16 g of 3-(4-phenyl-1,2,3,6-tetrahydro-1-pyridyl)-1-aminopropane are thus obtained, melting at 190° C.

Methyl 2-formylbenzoate may be prepared by the method described by E. L. ELIEL and A. W. BURGSTAHLER, J. Am. Chem. Soc., 71, 2251 (1949).

EXAMPLE 19

2.5 g of 2-acetylbenzoic acid is added to a solution of 3-(4-phenyl-1,2,3,6-tetrahydro-1-pyridyl)-1-aminopropane (7.8 g) in acetonitrile (90 cc) at a temperature close to 20° C. in the course of 10 minutes. Agitation is continued for 4 hours then 7.6 g of 3-(4-phenyl-1,2,3,6-tetrahydro-1-pyridyl)-1-aminopropane hydrochloride is added in the course of 30 minutes. Then 1.2 g of sodium cyanoborohydride is added to the suspension obtained, in the course of 5 minutes. Agitation is continued for 16 hours. The suspension is filtered and the precipitate washed with acetonitrile (20 cc). The organic extracts are combined, diluted with methylene chloride (200 cc) then washed with distilled water (120 cc), dried over anhydrous magnesium sulphate, treated with animal charcoal, filtered and concentrated to dryness under reduced pressure (20 mm Hg; 2.7 kPa) at 40° C. The residue obtained is poured onto alumina (750 g) contained in a column of 6 cm diameter. Elution is carried out with ethyl acetate (1000 cc) and the corresponding eluates are eliminated. Then elution is carried out with a mixture of ethyl acetate and methanol (98-2 by volume) (1000 cc) and the corresponding eluates are evaporated to dryness under reduced pressure (20 mm Hg; 2.7 kPa) at 50° C. The residue obtained is dissolved in methyl ethyl ketone (20 cc). A solution of oxalic acid (0.3 g) in methyl ethyl ketone (10 cc) is added and agitation continued for 1 hour at a temperature close to 20° C. The precipitate formed is separated by filtration and recrystallized from boiling acetonitrile (80 cc). 0.9.g of 3-methyl-2-[3-(4-phenyl-1,2,3,6-tetrahydro-1-pyridyl)-propyl]-1-isoindolinone oxalate are thus obtained, melting at 147° C.

EXAMPLE 20

16.5 cc of a 3N ethereal solution of phenylmagnesium bromide is added to an agitated solution of 2-[3-(4-phenyl-1,2,3,6-tetrahydro-1-pyridyl)propyl]phthalimide (8.6 g) in anhydrous tetrahydrofuran (80 cc) under inert atmosphere, in the course of 10 minutes and at a temperature close to 20° C. Agitation is continued for 3 hours then 200 cc of a saturated aqueous solution of ammonium chloride is added in the course of 15 minutes, maintaining the temperature in the neighbourhood of 20° C. The aqueous phase is extracted with methylene chloride (4×100 cc). The organic extracts are combined, dried over anhydrous magnesium sulphate, filtered and evaporated to dryness under reduced pressure (20 mm Hg; 2.7 kPa) at 40° C. The residue is dissolved in methylene chloride (10 cc) and poured onto silica (100 g) contained in a column of 4 cm diameter. Elution is carried out with a mixture of methylene chloride and methanol (98.5-1.5 by volume, 700 cc) and the corresponding eluate is evaporated to dryness under reduced pressure (20 mm Hg; 2.7 kPa) at 40° C. The precipitate obtained is recrystallized from boiling acetonitrile (10 cc). 2.6 g of 2-[3-(4-phenyl-1,2,3,6-tetrahydro-1-pyridyl)propyl]-3-phenyl-3-hydroxy-1-isoindolinone are thus obtained, melting at 123° C.

EXAMPLE 21

60 cc of trifluoroacetic acid is added in the course of 45 minutes to 2-[3-(4-phenyl-1,2,3,6-tetrahydro-1pyridyl)propyl]-3-phenyl-3-hydroxy-1-isoindolinone (12.4 g) and sodium cyanoborohydride (3.8 g) cooled to a temperature close to −25° C. Agitation is continued for 2 hours at a temperature close to 20° C. The solution is diluted with methylene chloride (150 cc) then washed with saturated aqueous sodium bicarbonate solution (130 cc). The aqueous phase is extracted with methylene chloride (4×100 cc). The organic extracts are combined, washed with 1N hydrochloric acid solution (3×50 cc), dried over anhydrous magnesium sulphate, treated with animal charcoal, filtered and concentrated to dryness under reduced pressure (20 mm Hg; 2.7 kPa) at 40° C. The residue obtained is dissolved in tetrahydrofuran (150 cc). Tetramethylethylenediamine (4.5 cc) is added and the solution heated to a temperature close to 65° C. for 1 hour. After cooling to a temperature close to 20° C., the solution is diluted with methylene chloride (300 cc), washed with distilled water (5×50 cc). The organic extract is dried over anhydrous magnesium sulphate, filtered and evaporated to dryness under reduced pressure (20 mm Hg; 2.7 kPa) at 50° C. The residue obtained is poured onto neutral alumina (750 g) contained in a column of 6 cm diameter. Elution is carried out with a mixture of ethyl acetate and cyclohexane (40-60 by volume) (2000 cc) and the corresponding eluates are eliminated. Elution is then carried out with ethyl acetate (3000 cc) and the corresponding eluates are evaporated to dryness under reduced pressure (20 mm Hg; 2.7 kPa) at 50° C. The residue obtained is dissolved in methyl ethyl ketone (30 cc). A solution of oxalic acid (0.7 g) in methyl ethyl ketone (10 cc) is added and agitation continued for 1 hour at a temperature close to 20° C. The precipitate formed is separated by filtration and recrystallized from boiling acetonitrile (240 cc). 1.6 g of 3-phenyl-2-[3-(4-phenyl-1,2,3,6-tetrahydro-1-pyridyl)propyl]-1-isoindolinone oxalate are obtained, melting at 198° C.

EXAMPLE 22

75 cc of trifluoroacetic acid is added in the course of 45 minutes to 2-[3-(4-phenyl-1,2,3,6-tetrahydro-1-pyridyl)propyl]-3-hydroxy-3-benzyl-1-isoindolinone (15.2 g) and sodium cyanoborohydride (4.6 g) cooled to a temperature close to −25° C. Agitation is continued for 4 hours at a temperature close to 20° C. The solution is diluted with methylene chloride (150 cc) then washed with saturated aqueous sodium bicarbonate solution (200 cc). The aqueous phase is extracted with methylene chloride (4×150 cc). The organic extracts are combined, washed with 1N hydrochloric acid solution (3×50 cc), dried over anhydrous magnesium sulphate, treated with animal charcoal, filtered and concentrated to dryness under reduced pressure (20 mm Hg; 2.7 kPa) at 40° C. The residue obtained is dissolved in tetrahydrofuran (150 cc). Tetramethylethylenediamine (3.1 cc) is added and the solution heated to a temperature close to 65° C. for 1 hour. After cooling to a temperature close to 20° C., the solution is diluted with methylene chloride (300 cc), and washed with distilled water (5×50 cc). The organic extract is dried over anhydrous magnesium sulphate, filtered and evaporated to dryness under reduced pressure (20 mm Hg; 2.7 kPa) at 50° C. The residue obtained is dissolved in acetonitrile (20 cc). A solution of oxalic acid (0.7 g) in acetonitrile (20 cc) is added and agitation is continued for 1 hour at a temperature close to 20° C. The precipitate formed is separated by filtration and recrystallized from boiling methanol (280 cc). 4.6 g of 3-benzyl-2-[3-(4-phenyl-1,2,3,6-tetrahydro-1-pyridyl)propyl]-1-isoindolinone oxalate are thus obtained, melting at 219° C.

2-[3-(4-Phenyl-1,2,3,6-tetrahydro-1-pyridyl)propyl]-3-benzyl-3-hydroxy-1-isoindolinone may be prepared in the following manner: a solution of benzylmagnesium bromide (75 cc), prepared from magnesium shavings (3.6 g) and benzyl bromide (19 g) in anhydrous tetrahydrofuran (75 cc), is added in the course of 30 minutes to an agitated solution under inert atmosphere of 2-[3-(4-phenyl-1,2,3,6-tetrahydro-1-pyridyl)phthalimide (17.3 g) in anhydrous tetrahydrofuran (100 cc) at a temperature close to 20° C. Agitation is continued for 3 hours, then 200 cc of a saturated aqueous solution of ammonium chloride is added in the course of 15 minutes, maintaining the temperature in the neighbourhood of 20° C. The aqueous phase is extracted with methylene chloride (5×100 cc). The organic extracts are combined, dried over anhydrous magnesium sulphate, filtered and evaporated to dryness under reduced pressure (20 mm Hg; 2.7 kPa) at 40° C. The residue is dissolved in ethyl acetate (50 cc) and poured onto silica (400 g) contained in a column of 8 cm diameter. Elution is carried out with ethyl acetate (800 cc) and the corresponding eluate is evaporated to dryness under reduced pressure (20 mm Hg; 2.7 kPa) at 40° C. 17.8 g of 2-[3-(4-phenyl-1,2,3,6-tetrahydro-1pyridyl)propyl]-3-benzyl-3-hydroxy-1-isoindolinone oxalate are obtained, whose Rf on a silica plate and in a mixture of methylene chloride and methanol (95-5 by volume) is 0.13.

EXAMPLE 23

The same procedure is followed as in Example 2, but starting from an agitated solution of 3-hydroxy-2-[3-(4-(4-hydroxyphenyl)-1-piperazinyl)propyl]-1-isoindolinone (4.6 g) in methanol (115 cc), to which 22.7 cc of concentrated sulphuric acid is added in the course of 15 minutes and at a temperature close to 20° C. Agitation is continued for 5 hours at a temperature close to 65° C. After cooling the solution to a temperature close to 0° C., 57 cc of a 33% aqueous solution of ammonia is added in the course of 1 hour. The precipitate formed is filtered and washed with methanol (50 cc). The filtrate is diluted with distilled water (200 cc) and a 33% aqueous solution of ammonia (50 cc) and extracted with methylene chloride (4×100 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (20 cc) and the solution is poured onto silica (500 g) contained in a column of 6 cm diameter. Elution is carried out with a mixture of methylene chloride and methanol (97-3 by volume). The first 800 cc are eliminated and the next 3000 cc are evaporated to dryness under reduced pressure (20 mm Hg; 2.7 kPa) at 50° C. The residue obtained is dissolved in methyl ethyl ketone (35 cc). A solution of oxalic acid (0.8 g) in methyl ethyl ketone (20 cc) is added, and agitation continued for 1 hour at a temperature close to 20° C. The precipitate formed is separated by filtration and recrystallized from boiling acetonitrile (200 cc). 1.4 g of 3-methoxy-2-[3-(4-(4-hydroxyphenyl)-1-piperazinyl)propyl]-1-isoindolinone oxalate are thus obtained, melting at 147° C.

3-Hydroxy-2-[3-(4-(4-hydroxyphenyl)-1-piperazinyl)-propyl]-1-isoindolinone may be prepared as described in Example 3 for the preparation of 2-[3-(4-phenyl-1,2,3,6-tetrahydro-1-pyridyl)propyl]-3-hydroxy-1-isoindolinone, but starting from an agitated solution of 2-[3-(4-(4-hydroxyphenyl)-1-piperazinyl)propyl]phthalimide (12.3 g) in methanol (350 cc) and distilled water (35 cc), to which potassium borohydride (1.8 g) is added at a temperature close to 20° C. Agitation is continued for 24 hours. The solution obtained is poured into distilled water (200 cc) and extracted with methylene chloride (4×100 cc). The organic extracts are combined, dried over anhydrous magnesium sulphate, filtered and concentrated to dryness under reduced pressure (20 mm Hg; 2.7 kPa) at 40° C. The residue obtained is dissolved in boiling methyl ethyl ketone (30 cc). After cooling to a temperature close to 20° C., the precipitate formed is separated by filtration. 4.9 g of 3-hydroxy-2-[3-(4-(4-hydroxyphenyl)-1-piperazinyl)propyl]-1-isoindolinone are thus obtained, melting at 190° C.

2-3-(4-(4-hydroxyphenyl)-1-piperazinyl)propyl]phthalimide may be prepared as described in Example 3 for the preparation of 2-[3-(4-phenyl-1,2,3,6-tetrahydro-1-pyridyl)propyl]phthalimide, but starting from an agitated solution of 2-(3-bromopropyl)phthalimide (18 g) and 4-(4-hydroxyphenyl)piperazine (17.4 g) in toluene (300 cc) to which 19 cc of triethylamine is added in the course of 10 minutes and at a temperature close to 20° C. The precipitate obtained is dissolved in methylene chloride (50 cc) and poured onto silica (2000 g) contained in a column of 8 cm diameter. Elution is carried out with mixture of methylene chloride and methanol (98-2 by volume). The first 3000 cc are eliminated and the eluates corresponding to the next 1500 cc are concentrated to dryness under reduced pressure (20 mm Hg; 2.7 kPa) at 50° C. 12.3 g of an orangey oil are obtained, whose Rf on a silica plate and in a mixture of methylene chloride and methanol (95-5 by volume) is 0.3.

The present invention also provides pharmaceutical compositions comprising a compound of formula (I), as the free base or as an addition salt with a pharmaceutically acceptable acid, in association with any other pharmaceutically compatible product, which may be inert or physiologically active, and more particularly a pharmaceutically acceptable carrier or coating. The compositions according to the invention may be administered orally, parenterally, rectally or topically.

As solid compositions for oral administration, tablets, pills, powders (e.g. in gelatine capsules or cachets) or granules may be used. In these compositions, the active principle according to the invention is mixed with one or more inert diluents, such as starch, cellulose, sucrose, lactose or silica. These compositions may also include substances other than the diluents, e.g. one or more lubricants such as magnesium stearate or talc, colouring matter, a coating (sugared pills) or a varnish.

As liquid compositions for oral administration, pharmaceutically acceptable solutions, suspensions, emulsions, syrups and elixirs may be used containing inert diluents such as water, ethanol, glycerol, vegetable oils or paraffin oil. These compositions may include substances other than diluents e.g. wetting, sweetening, thickening, aromatizing or stabilizing products.

Sterile compositions for parenteral administration may be aqueous or non-aqueous solutions, suspensions or emulsions. As solvent or vehicle, water, propylene glycol, a polyethylene glycol, vegetable oils, particularly olive oil, injectable organic esters, e.g. ethyl oleate, or other suitable organic solvents may be used. These compositions may also contain adjuvants, in particular wetting agents, isotonicity agents, emulsifiers, dispersants and stabilizers. Sterilization may be carried out in a number of ways, e.g. by aseptisicing filtration, by incorporating sterilization agents in the composition, by irradiation or by heating. They may also be prepared in the form of sterile solid compositions, which may be dissolved at the moment of use in an injectable sterile medium.

Compositions for rectal administration are suppositories or rectal capsules, which besides the active principle contain excipients such as cocoa butter, semisynthetic glycerides or polyethylene glycols.

Compositions for topical application may for example be creams, ointments, lotions, eye washes, mouth washes, nasal drops or aerosols.

In human therapeutics, the compounds according to the invention are useful for the treatment of diseases in which serotonin is involved and particularly diseases of the central nervous system, of the cardiovascular system and gastrointestinal disorders. They are, in particular, useful for the treatment of anxiety, sleep disorders, depression, psychoses, especially schizophrenia, migraine, asthma, hypertension and urticaria, as analgesics and as inhibitors of platelet aggregation.

The doses depend on the required effect, the duration of treatment and the mode of administration; they are generally between 10 and 300 mg per day taken orally for an adult with unitary doses from 2 to 100 mg of active substance.

In a general way, the doctor will determine the appropriate dosage in relation to age, weight and all the other factors relevant to the patient to be treated.

The following Examples illustrate compositions according to the invention:

EXAMPLE A

Capsules rated at 50 mg of active product, having the following composition, are prepared in the customary way:

| | |
|---|---|
| 3-Methoxy-2[3-(4-(4-fluorophenyl)-1,2,3,6-tetrahydro-1-pyridyl)-propyl]-1-isoindolinone | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets rated at 50 mg of active product, having the following composition, are prepared in the customary way:

| | |
|---|---|
| 3-Methoxy-2[3-(4-(4-fluorophenyl)-1,2,3,6-tetrahydro-1-pyridyl)-propyl]-1-isoindolinone | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol, titanium oxide (72-3.5-24.5) q.s. 1 tablet film coated finished at | 245 mg |

EXAMPLE C

An injectable solution, rated at 10 mg of active product, having the following composition, is prepared in the customary way:

| | |
|---|---|
| 3-Methyl-2-[3-(4-phenyl-1,2,3,6-tetrahydro-1-pyridyl)-propyl]-1-isoindolinone | 10 mg |
| Benzoic acid | 80 mg |
| Benzyl alcohol | 0.06 cc |
| Sodium benzoate | 80 mg |

| | |
|---|---|
| -continued | |
| Ethanol (95%) | 0.4 cc |
| Sodium hydroxide | 24 mg |
| Propylene glycol | 1.6 cc |
| Water | q.s. to 4 cc |

We claim:

1. A compound of formula

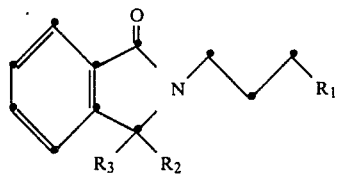

in which
either $R_1$ represents 4-phenyl-1,2,3,6-tetrahydro-1-pyridyl or 4-(4-fluorophenyl)-1,2,3,6-tetrahydro-1-pyridyl, $R_2$ represents hydrogen, alkoxy of 1 or 2 carbon atoms, hydroxyl, alkyl, alkylthio, alkylcarbonyloxy, phenylalkylcarbonyloxy, phenylalkyl or —$NR_4R_5$ in which $R_4$ represents hydrogen or alkyl and $R_5$ represents alkyl, phenyl, monohalogenated phenyl or pyridyl, and $R_3$ represents hydrogen, or else $R_2$ represents phenyl and $R_3$ represents hydrogen or hydroxyl;

or $R_1$ represents a 4-phenyl-1-piperazinyl radical whose phenyl nucleus is substituted in the 4-position by halogen or hydroxyl, $R_2$ represents alkoxy and $R_3$ represents hydrogen;

provided that when $R_1$ represents 4-phenyl-1,2,3,6-tetrahydro-1-pyridyl, $R_2$ is not hydroxyl and that unless otherwise stated, the alkyl and alkoxy radicals and the alkyl and alkoxy portions contain 1 to 4 carbon atoms each in a straight or branched chain, and pharmaceutically acceptable addition salts thereof formed with an inorganic or organic acid.

2. A compound according to claim 1 in which:
either $R_1$ represents 4-phenyl-1,2,3,6-tetrahydro-1-pyridyl, or 4-(4-fluorophenyl)-1,2,3,6-tetrahydro-1-pyridyl, $R_2$ represents alkoxy, hydroxyl, alkyl, alkylthio, or alkylcarbonyloxy and $R_3$ represents hydrogen, or $R_1$ represents 4-(4-fluorophenyl)-1-piperazinyl, $R_2$ represents alkoxy and $R_3$ represents hydrogen,
and pharmaceutically acceptable addition salts thereof formed with an inorganic or organic acid.

3. A compound according to claim 1 which is 3-methoxy-2-[3-(4-(4-fluorophenyl)-1,2,3,6-tetrahydro-1-pyridyl)propyl]-1-isoindolinone and its pharmaceutically acceptable acid addition salts.

4. A compound according to claim 1 which is 3-methoxy-2-[3-(4-(4-fluorophenyl)-1-piperazinyl)-propyl]-1-isoindolinone and its pharmaceutically acceptable acid addition salts.

5. A compound according to claim 1 which is 3-methoxy-2-[3-(4-phenyl-1,2,3,6-tetrahydro-1-pyridyl)-propyl]-1-isoindolinone and its pharmaceutically acceptable acid addition salts.

6. A compound according to claim 1 which is 3-ethoxy-2-[3-(4-phenyl-1,2,3,6-tetrahydro-1-pyridyl)-propyl]-1-isoindolinone and its pharmaceutically acceptable acid addition salts.

7. A compound according to claim 1 which is 3-methylthio-2-[3-(4-phenyl-1,2,3,6-tetrahydro-1-pyridyl)-propyl]-1-isoindolinone and its pharmaceutically acceptable acid addition salts.

8. A compound according to claim 1 which is 3-methyl-2[3-(4-phenyl-1,2,3,6-tetrahydro-1-pyridyl)propyl]-1-isoindolinone and its pharmaceutically acceptable acid addition salts.

9. A compound according to claim 1 which is 3-acetoxy-2-[3-(4-phenyl-1,2,3,6-tetrahydro-1-pyridyl)-propyl]-1-isoindolinone and its pharmaceutically acceptable acid addition salts.

10. A compound according to claim 1 which is 3-hydroxy-2-[3-(4-(4-fluorophenyl)-1,2,3,6-tetrahydro-1-pyridyl)propyl]-1-isoindolinone and its pharmaceutically acceptable acid addition salts.

11. A pharmaceutical composition for treating a disease ameliorated by the blocking of serotonin receptors which comprises a compound according to claim 1 or an addition salt thereof with a pharmaceutically acceptable carrier or coating.

12. A pharmaceutical composition for treating a disease ameliorated by the blocking of serotonin receptors which comprises a compound according to claim 2 or an addition salt thereof with a pharmaceutically acceptable acid, in association with a pharmaceutically acceptable carrier or coating.

13. A method of treating a disease ameliorated by the blocking of serotonin receptors which comprises administering to a subject capable of benefitting from such treatment an effective amount of a compound of formula (I) as defined in claim 1 or of a pharmaceutically acceptable salt thereof.

14. A method according to claim 13 for the treatment of anxiety, schizophrenia, depression, migraine, asthma, hypertension or urticaria, for producing an analgesic effect, or for inhibiting platelet aggregation.

* * * * *